(12) United States Patent
Wang

(10) Patent No.: US 6,876,886 B1
(45) Date of Patent: Apr. 5, 2005

(54) MAGNETICALLY SHIELDED CONDUCTOR

(75) Inventor: Xingwu Wang, Wellsville, NY (US)

(73) Assignee: Nandset, LLC, East Rochester, NY (US)

(*) Notice: Subject to any disclaimer, the term of this patent is extended or adjusted under 35 U.S.C. 154(b) by 338 days.

(21) Appl. No.: 10/229,183

(22) Filed: Aug. 26, 2002

Related U.S. Application Data

(63) Continuation-in-part of application No. 10/054,407, filed on Jan. 22, 2002, now Pat. No. 6,506,972.

(51) Int. Cl.[7] .................. A61B 5/0408; A61N 1/05; H01B 11/06
(52) U.S. Cl. .................. 607/119; 607/116; 600/374; 174/36; 333/12
(58) Field of Search ................. 607/115–156; 600/373–381; 606/13–52; 174/36, 113 R, 102 SC, 102 P; 333/12, 243

(56) References Cited

U.S. PATENT DOCUMENTS 5,452,720 A * 9/1995 Smith et al. ............. 600/427
6,102,885 A * 8/2000 Bass ...................... 604/22
6,506,972 B1 * 1/2003 Wang ..................... 174/36

* cited by examiner

*Primary Examiner*—Jeffrey R. Jastrzab
(74) *Attorney, Agent, or Firm*—Howard J. Greenwald

(57) ABSTRACT

A magnetically shielded conductor assembly containing a conductor disposed within an insulating matrix, and nanomagentic material and nanoelectrical material disposed around the conductor. The conductor has a resistivity at 20 degrees Centigrade of from about 1 to about 100 microohm-centimeters. The insulating matrix is composed of nano-sized particles having a maximum dimension of from about 10 to about 100 nanometers. The insulating matrix has a resistivity of from about 1,000,000,000 to about 10,000,000,000,000 ohm-centimeter. The nanomagnetic material has an average particle size of less than about 100 nanometers. The nanomagnetic material has a saturation magnetization of from about 200 to about 26,000 Gauss. The magnetically shielded conductor assembly is flexible, having a bend radius of less than 2 centimeters.

19 Claims, 9 Drawing Sheets

MAGNETICALLY SHIELDED CONDUCTOR

REFERENCE TO RELATED PATENT APPLICATION

This application is a continuation-in-part of applicant's patent application U.S. Ser. No. 10/054,407, filed on Jan. 22, 2002 now U.S. Pat. No. 6,506,972.

FIELD OF THE INVENTION

A conductor assembly comprised of a conductor disposed within an insulating sheath, wherein the sheath is coated with nanomagnetic material and nanoelectrical material.

BACKGROUND OF THE INVENTION

Many implanted medical devices that are powered by electrical energy have been developed. Most of these devices comprise a power source, one or more conductors, and a load.

When a patient with one of these implanted devices is subjected to high intensity magnetic fields, currents are often induced in the implanted conductors. The large current flows so induced often create substantial amounts of heat. Because living organisms can generally only survive within a relatively narrow range of temperatures, these large current flows are dangerous.

Furthermore, implantable devices, such as implantable pulse generators (IPGs) and cardioverter/defibrillator/pacemaker (CDPs), are sensitive to a variety of forms of electromagnetic interference (EMI). These devices include sensing and logic systems that respond to low-level signals from the heart. Because the sensing systems and conductive elements of these implantable devices are responsive to changes in local electromagnetic fields, they are vulnerable to external sources of severe electromagnetic noise, and in particular to electromagnetic fields emitted during magnetic resonance imaging (MRI) procedures. Therefore, patients with implantable devices are generally advised not to undergo magnetic resonance imaging (MRI) procedures, which often generate magnetic fields of from between about 1 about 20 Teslas.

One additional problem with implanted conductors is that, when they are conducting electricity and are simultaneously subjected to large magnetic fields, a Lorentz force is created which often causes the conductor to move. This movement may damage body tissue.

In U.S. Pat. No. 4,180,600, there is disclosed and claimed a fine magnetically shielded conductor wire consisting of a conductive copper core and a magnetically soft alloy metallic sheath metallurgically secured to the conductive core, wherein the sheath consists essentially of from 2 to 5 weight percent of molybdenum, from about 15 to about 23 weight percent of iron, and from about 75 to about 85 weight percent of nickel. Although the device of this patent does provide magnetic shielding, it still creates heat when it interacts with strong magnetic fields.

It is an object of this invention to provide a conductor assembly, which is shielded from large magnetic fields, which does not create large amounts of heat in the presence of such fields, and which does not exhibit the Lorentz effect when subjected to such fields.

SUMMARY OF THE INVENTION

In accordance with this invention, there is provided a magnetically shielded conductor assembly comprised of a conductor disposed within an insulating matrix, wherein said insulating matrix is coated with a nanomagnetic particulate material.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
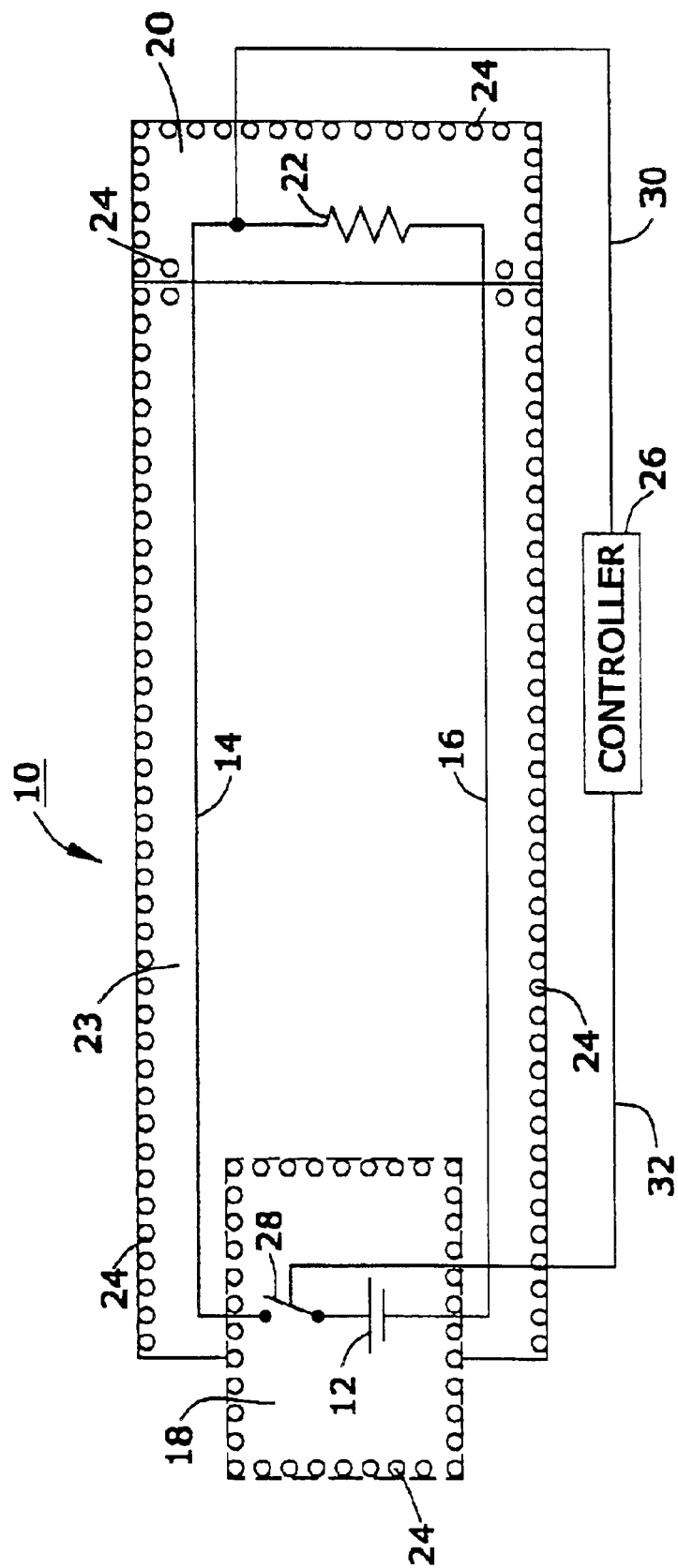
FIG. 1 is a schematic sectional view of a shielded implanted device comprised of one preferred conductor assembly of the invention.

FIG. 1 is a schematic sectional view of one preferred device 10 that, in one embodiment, is implanted in a living organism. Referring to FIG. 1, it will be seen that device 10 is comprised of a power source 12, a first conductor 14, a second conductor 16, a first insulative shield 18 disposed about power source 12, a second insulative shield 20 disposed about a load 22, a third insulative shield 23 disposed about a first conductor 14, and a second conductor 16, and a multiplicity of nanomagentic particles 24 disposed on said first insulative shield, said second insulative shield, and said third insulative shield.

In the embodiment depicted in FIG. 1, the power source 12 is a battery 12 that is operatively connected to a controller 26. In the embodiment depicted, controller 26 is operatively connected to the load 22 and the switch 28. Depending upon the information furnished to controller 26, it may deliver no current, direct current, and/or current pulses to the load 22.

In one embodiment, not shown, the controller 26 and/or the wires 30 and 32 are shielded from magnetic radiation. In another embodiment, not shown, one or more connections between the controller 26 and the switch 28 and/or the load 22 are made by wireless means such as, e.g., telemetry means.

In one embodiment, not shown, the power source 12 provides a source of alternating current. In another embodiment, the power source 12 in conjunction with the controller 26 provides pulsed direct current.

The load 22 may be any of the implanted devices known to those skilled in the art. Thus, e.g., load 22 may be a pacemaker. Thus, e.g., load 22 may be an artificial heart. Thus, e.g., load 22 may be a heart-massaging device. Thus, e.g., load 22 may be a defibrillator.

The conductors 14 and 16 may be any conductive material (s) that have a resistivity at 20 degrees Centigrade of from about 1 to about 100 microohm-centimeters. Thus, e.g., the conductive material(s) may be silver, copper, aluminum, alloys thereof, mixtures thereof, and the like.

In one embodiment, the conductors 14 and 16 consist essentially of such conductive material. Thus, e.g., it is preferred not to use, e.g., copper wire coated with enamel. The use of such typical enamel coating on the conductor does not work well in the instant invention.

In the first step of the process of this invention, step 40, the conductive wires 14 and 16 are coated with electrically insulative material. Suitable insulative materials include nano-sized silicon dioxide, aluminum oxide, cerium oxide, yttrium-stabilized zirconia, silicon carbide, silicon nitride, aluminum nitride, and the like. In general, these nano-sized particles will have a particle size distribution such that at least about 90 weight percent of the particles have a maximum dimension in the range of from about 10 to about 100 nanometers.

The coated conductors 14 and 16 may be prepared by conventional means such as, e.g., the process described in U.S. Pat. No. 5,540,959, the entire disclosure of which is hereby incorporated by reference into this specification. This patent describes and claims a process for preparing a coated substrate, comprising the steps of: (a) creating mist particles from a liquid, wherein: 1. said liquid is selected from the group consisting of a solution, a slurry, and mixtures thereof, 2. said liquid is comprised of solvent and from 0.1 to 75 grams of solid material per liter of solvent, 3. at least 95 volume percent of said mist particles have a maximum dimension less than 100 microns, and 4. said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist particles to a temperature of at least about 100 degrees centigrade, thereby producing a heated vapor; (d) depositing said heated vapor onto a substrate, thereby producing a coated substrate; and (e) subjecting said coated substrate to a temperature of from about 450 to about 1,400 degrees centigrade for at least about 10 minutes.

By way of further illustration, one may coat conductors 14 and 16 by means of the processes disclosed in a text by D. Satas on "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like.

Figure 2:
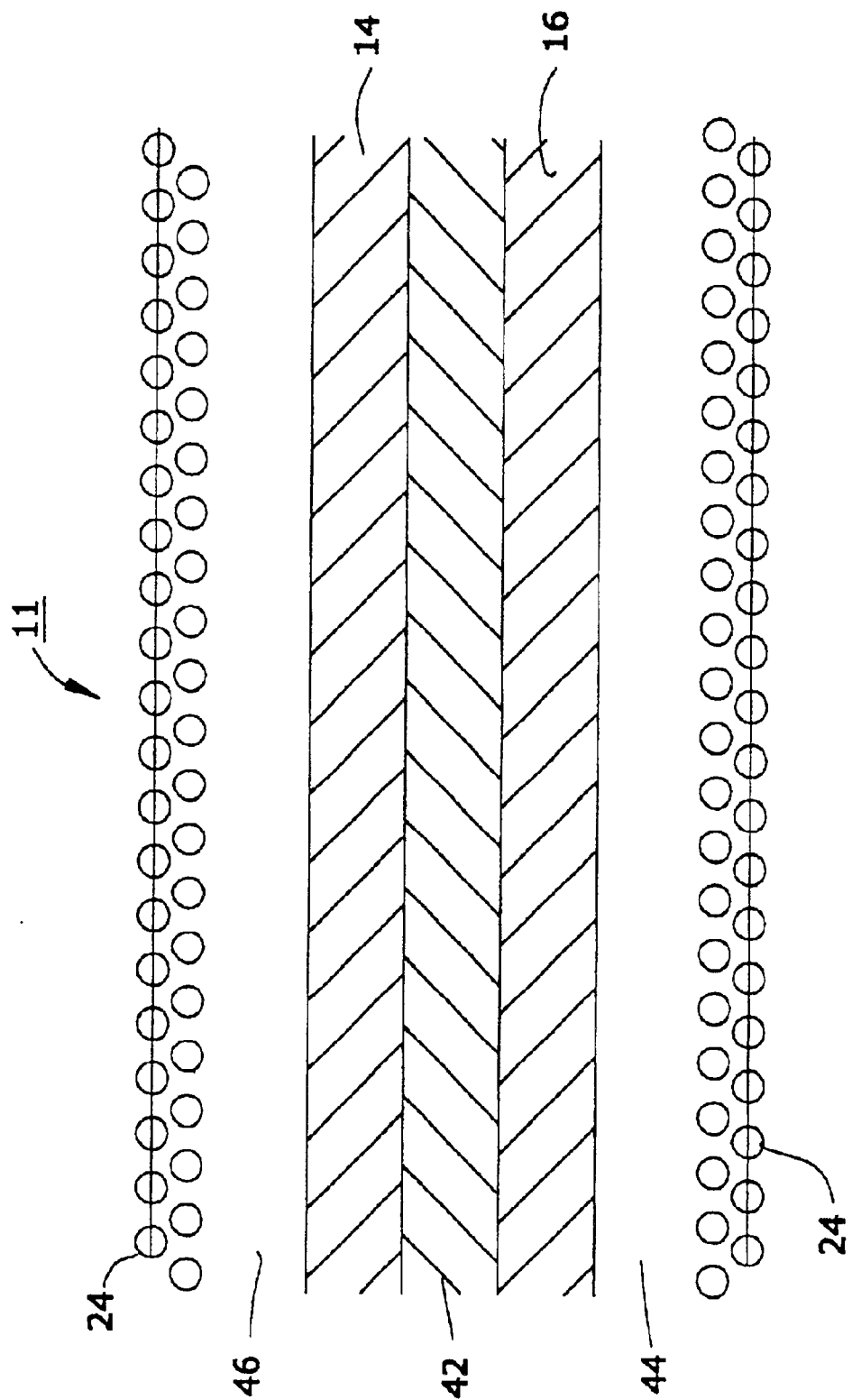
FIG. 2 is an enlarged sectional view of a portion of the conductor assembly of FIG. 1.

FIG. 2 is a sectional view of the coated conductors 14/16 of the device of FIG. 1. Referring to FIG. 2, it will be seen that conductors 14 and 16 are separated by insulating material 42. In order to obtain the structure depicted in FIG. 2, one may simultaneously coat conductors 14 and 16 with the insulating material so that such insulators both coat the conductors 14 and 16 and fill in the distance between them with insulation.

The insulating material 42 that is disposed between conductors 14/16, may be the same as the insulating material 44146 that is disposed above conductor 14 and below conductor 16. Alternatively, and as dictated by the choice of processing steps and materials, the insulating material 42 may be different from the insulating material 44 and/or the insulating material 46. Thus, step 48 of the process describes disposing insulating material between the coated conductors 14 and 16. This step may be done simultaneously with step 40; and it may be done thereafter.

The insulating material 42, the insulating material 44, and the insulating material 46 each generally has a resistivity of from about 1,000,000,000 to about 10,000,000,000,000 ohm-centimeters.

After the insulating material 42/44/46 has been deposited, and in one embodiment, the coated conductor assembly is preferably heat treated in step 50. This heat treatment often is used in conjunction with coating processes in which the heat is required to bond the insulative material to the conductors 14/16.

The heat-treatment step may be conducted after the deposition of the insulating material 42/44/46, or it may be conducted simultaneously therewith. In either event, and when it is used, it is preferred to heat the coated conductors 14/16 to a temperature of from about 200 to about 600 degrees Centigrade for from about 1 minute to about 10 minutes.

Figure 1A:
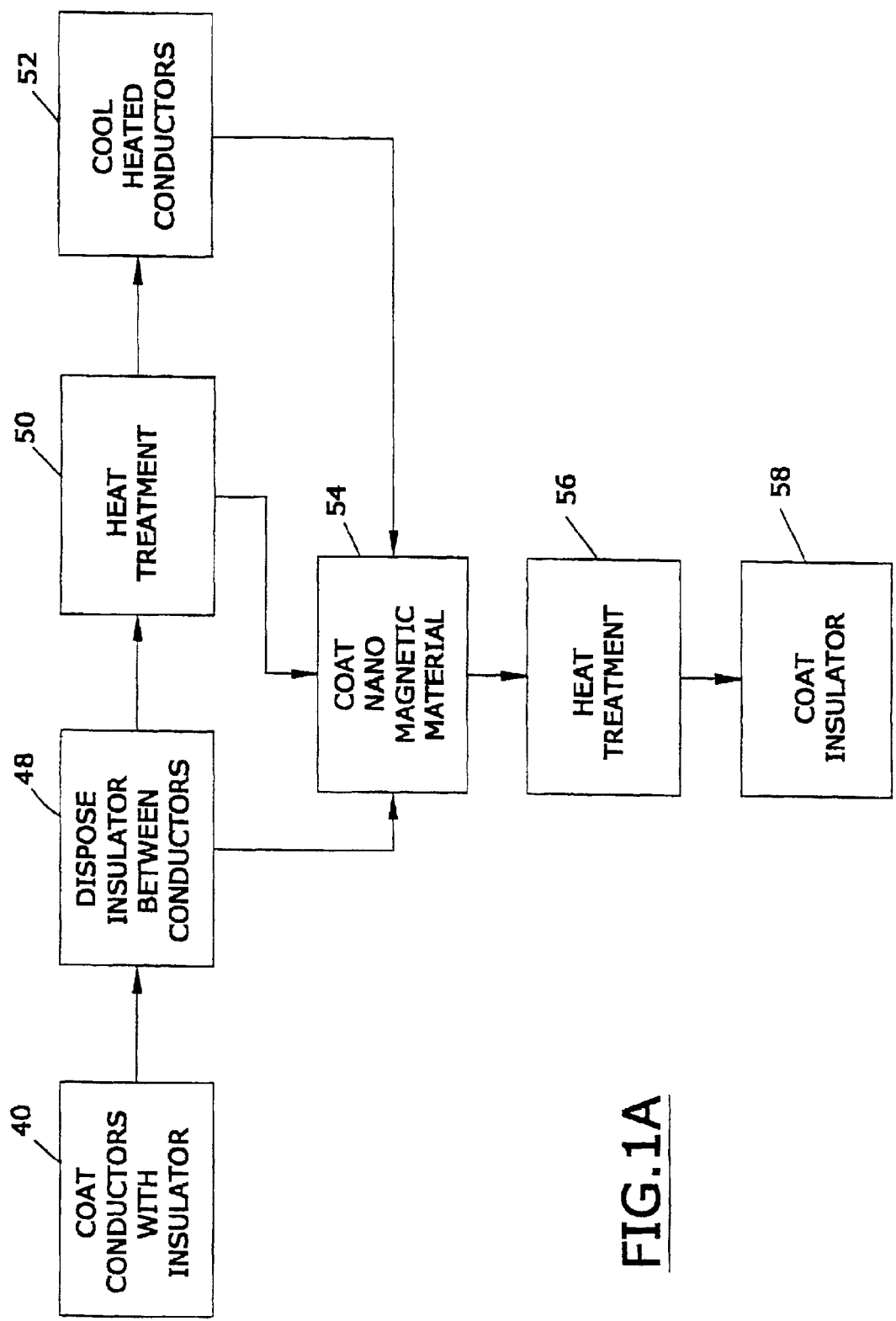
FIG. 1A is a flow diagram of a preferred process of the invention.

Referring again to FIG. 1A, and in step 52 of the process, after the coated conductors 14/16 have been subjected to heat treatment step 50, they are allowed to cool to a temperature of from about 30 to about 100 degrees Centigrade over a period of time of from about 3 to about 15 minutes.

One need not invariably heat treat and/or cool. Thus, referring to FIG. 1A, one may immediately coat nanomagnetic particles onto to the coated conductors 14/16 in step 54 either after step 48 and/or after step 50 and/or after step 52.

In step 54, nanomagnetic materials are coated onto the previously coated conductors 14 and 16. This is best shown in FIG. 2, wherein the nanomagnetic particles are identified as particles 24.

In general, and as is known to those skilled in the art, nanomagnetic material is magnetic material which has an average particle size less than 100 nanometers and, preferably, in the range of from about 2 to 50 nanometers. Reference may be had, e.g., to U.S. Pat. No. 5,889,091 (rotationally free nanomagnetic material), U.S. Pat. Nos. 5,714,136, 5,667,924, and the like. The entire disclosure of each of these United States patents is hereby incorporated by reference into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, chromium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. De Marco, X. W. Wang, et al. on "Mossbauer and magnetization studies of nickel ferrites" published in the Journal of Applied Physics 73(10), May 15, 1993, at pages 6287–6289.

In general, the thickness of the layer of nanomagnetic material deposited onto the coated conductors 14/16 is less than about 5 microns and generally from about 0.1 to about 3 microns.

After the nanomagnetic material is coated in step 54, the coated assembly may be optionally heat-treated in step 56. In this optional step 56, it is preferred to subject the coated conductors 14/16 to a temperature of from about 200 to about 600 degrees Centigrade for from about 1 to about 10 minutes.

Figure 3:
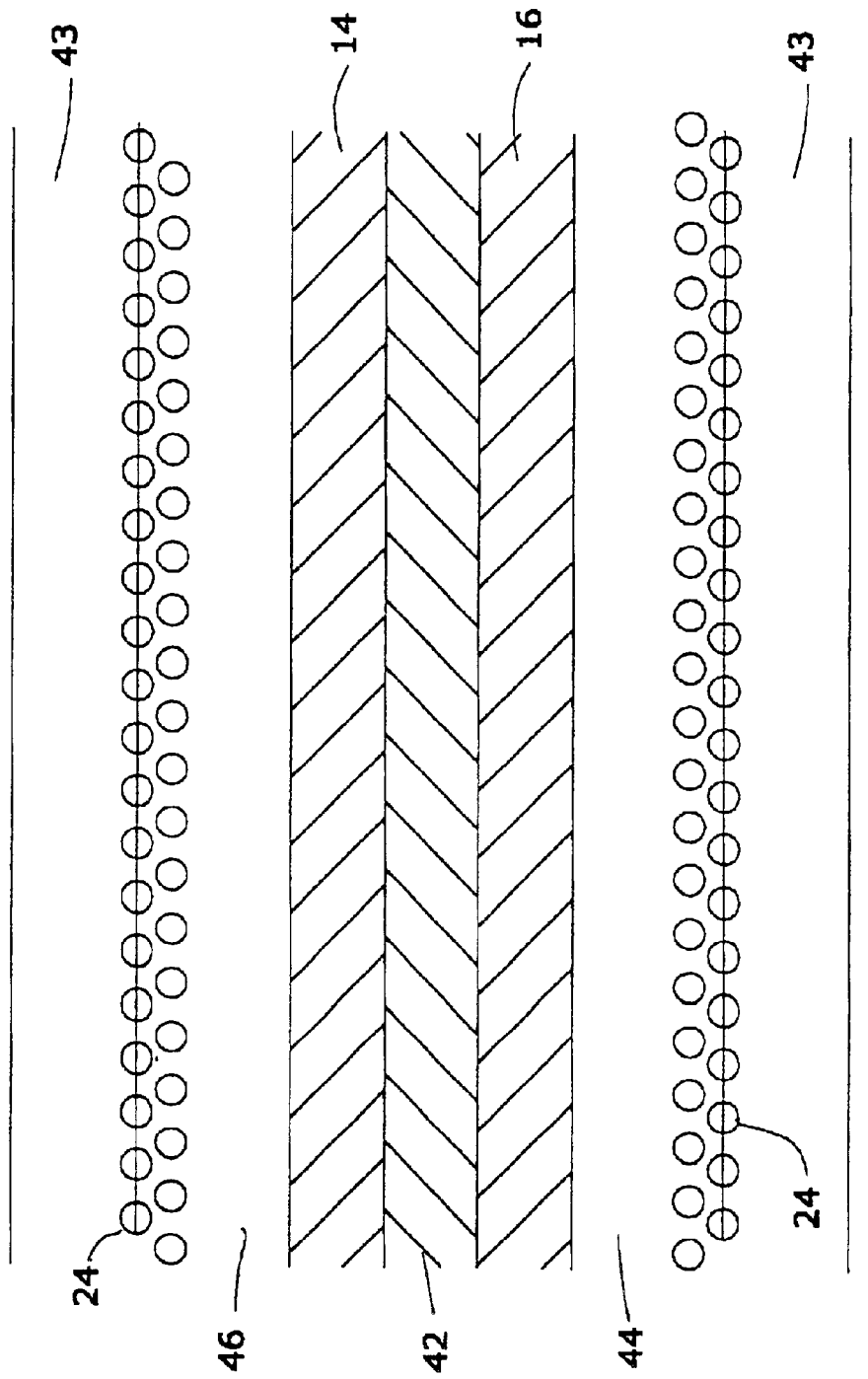
FIG. 3 is a sectional view of another conductor assembly of this invention.

In one embodiment, illustrated in FIG. 3, one or more additional insulating layers 43 are coated onto the assembly depicted in FIG. 2, by one or more of the processes disclosed hereinabove. This is conducted in optional step 58 (see FIG. 1A).

Figure 4:
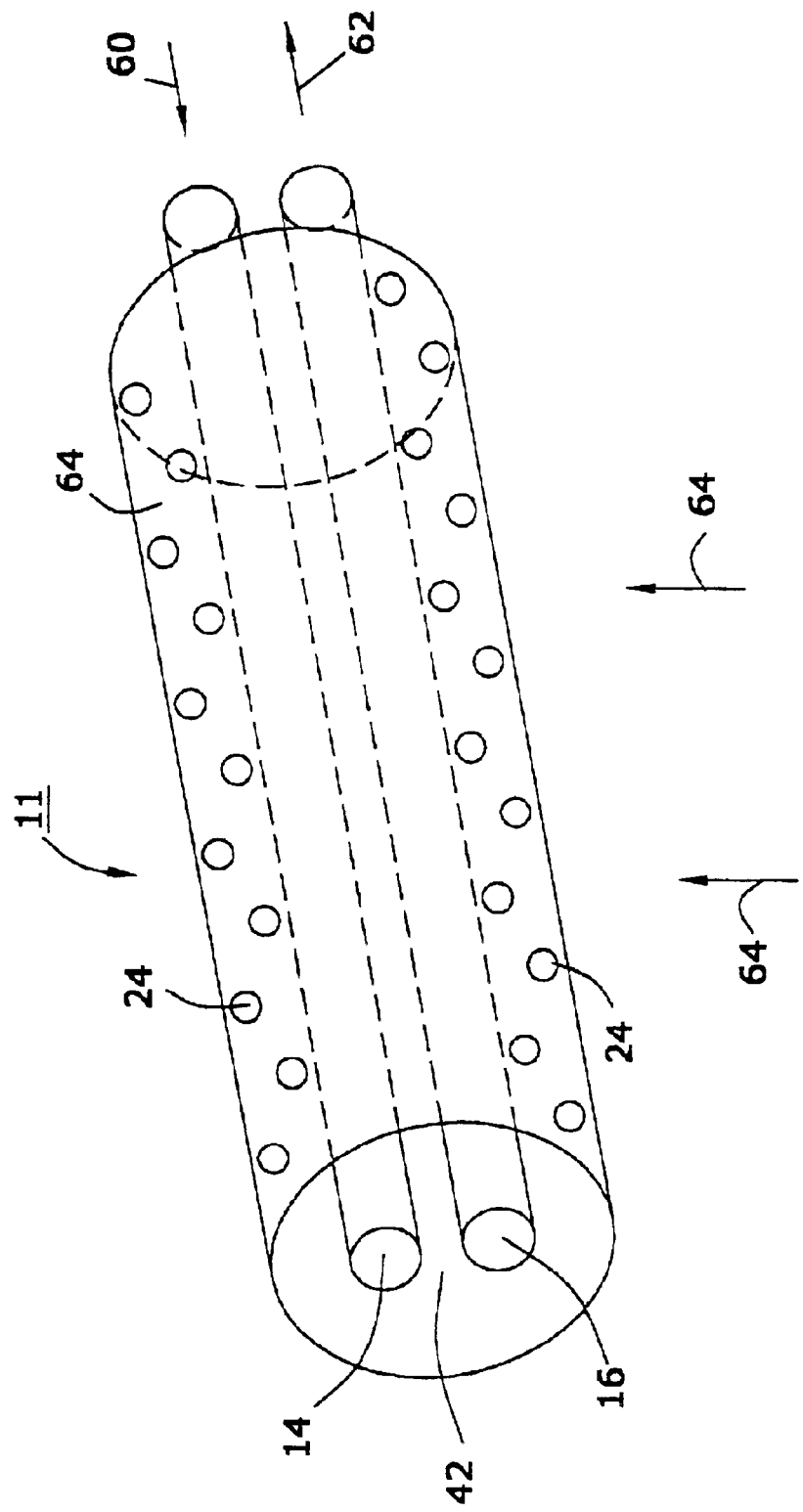
FIG. 4 is a schematic view of the conductor assembly of FIG. 2.

FIG. 4 is a partial schematic view of the assembly 11 of FIG. 2, illustrating the current flow in such assembly. Referring go FIG. 4, it will be seen that current flows into conductor 14 in the direction of arrow 60, and it flows out of conductor 16 in the direction of arrow 62. The net current flow through the assembly 11 is zero; and the net Lorentz force in the assembly 11 is thus zero. Consequently, even high current flows in the assembly 11 do not cause such assembly to move.

In the embodiment depicted in FIG. 4, conductors 14 and 16 are substantially parallel to each other. As will be apparent, without such parallel orientation, there may be some net current and some net Lorentz effect.

In the embodiment depicted in FIG. 4, and in one preferred aspect thereof, the conductors 14 and 16 preferably have the same diameters and/or the same compositions and/or the same length.

Referring again to FIG. 4, the nanomagnetic particles 24 are present in a density sufficient so as to provide shielding from magnetic flux lines 64. Without wishing to be bound to any particular theory, applicant believes that the nanomagnetic particles 24 trap and pin the magnetic lines of flux 64.

In order to function optimally, the nanomagnetic particles 24 have a specified magnetization. As is known to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

Referring again to FIG. 4, the layer of nanomagnetic particles 24 preferably has a saturation magnetization, at 25 degrees Centigrade, of from about 200 to about 25,000 Gauss, or higher. In one embodiment, the saturation magnetization at room temperature of the nanomagentic particles is from about 500 to about 10,000 Gauss. For a discussion of the saturation magnetization of various materials, reference may be had, e.g., to U.S. Pat. Nos. 4,705,613, 4,631,613, 5,543,070, 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagentic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film has a saturation magnetization of 24,000 Gauss.

By the appropriate selection of nanomagnetic particles, and the thickness of the films deposited, one may obtain saturation magnetizations of as high as at least about 26,000.

In the preferred embodiment depicted in FIG. 4, the nanomagnetic particles 24 are disposed within an insulating matrix so that any heat produced by such particles will be slowly dispersed within such matrix. Such matrix, as indicated hereinabove, may be made from ceria, calcium oxide, silica, alumina. In general, the insulating material 42 preferably has a thermal conductivity of less than about 20 (caloriescentimeters/square centimeters–degree second)× 10,000. See, e.g., page E-6 of the $63^{rd}$ Edition of the "Handbook of Chemistry and Physics" (CRC Press, Inc., Boca Raton, Fla., 1982).

The nanomagnetic materials 24 typically comprise one or more of iron, cobalt, nickel, gadolinium, and samarium atoms. Thus, e.g., typical nanomagnetic materials include alloys of iron and nickel (permalloy), cobalt, niobium, and zirconium (CNZ), iron, boron, and nitrogen, cobalt, iron, boron, and silica, iron, cobalt, boron, and fluoride, and the like. These and other materials are descried in a book by J. Douglas Adam et al. entitled "Handbook of Thin Film Devices" (Academic Press, San Diego, Calif., 2000). Chapter 5 of this book beginning at page 185, describes "magnetic films for planar inductive components and devices;" and Tables 5.1 and 5.2 in this chapter describe many magnetic materials.

Figure 5:
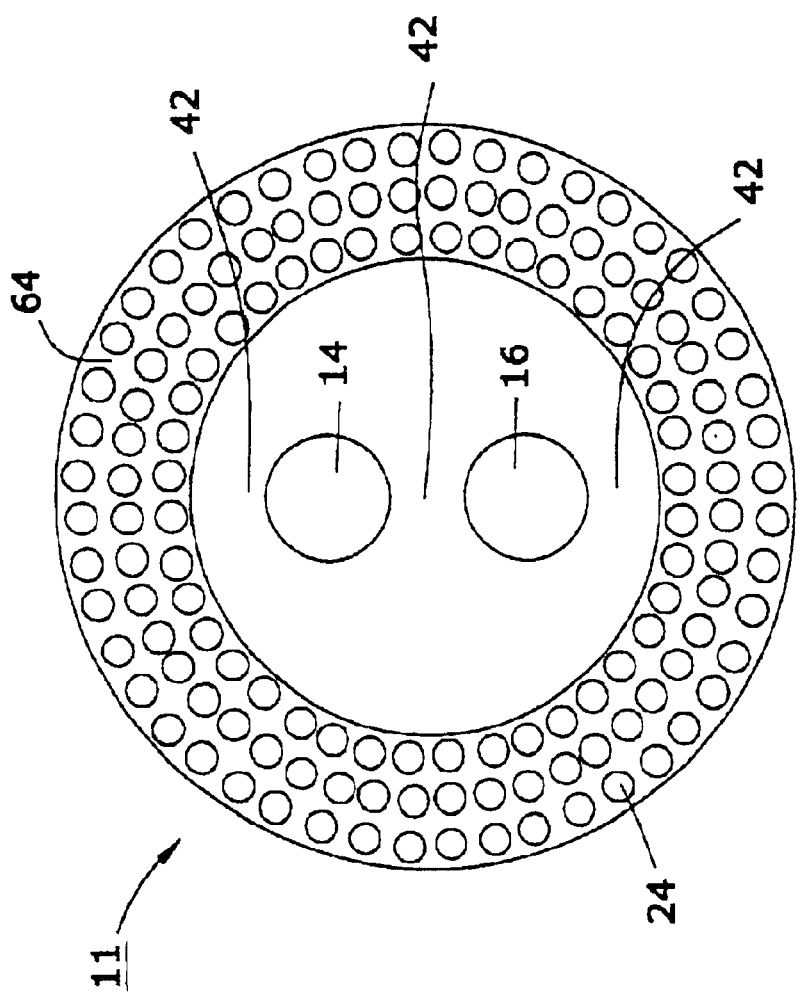
FIG. 5 is a sectional view of the conductor assembly of FIG. 2.

FIG. 5 is a sectional view of the assembly 11 of FIG. 2. The device of FIG. 5, and of the other Figures of this application, is preferably substantially flexible. As used in this specification, the term flexible refers to an assembly that can be bent to form a circle with a radius of less than 2 centimeters without breaking. Put another way, the bend radius of the coated assembly 11 can be less than 2 centimeters. Reference may be had, e.g., to U.S. Pat. Nos. 4,705,353, 5,946,439, 5,315,365, 4,641,917, 5,913,005, and the like. The entire disclosure of each of these United States patents is hereby incorporated by reference into this specification.

As will be apparent, even when the magnetic insulating properties of the assembly of this invention are not 100 percent effective, the assembly still prevents the rapid dissipation of heat to bodily tissue.

Figures 6A, 6B:
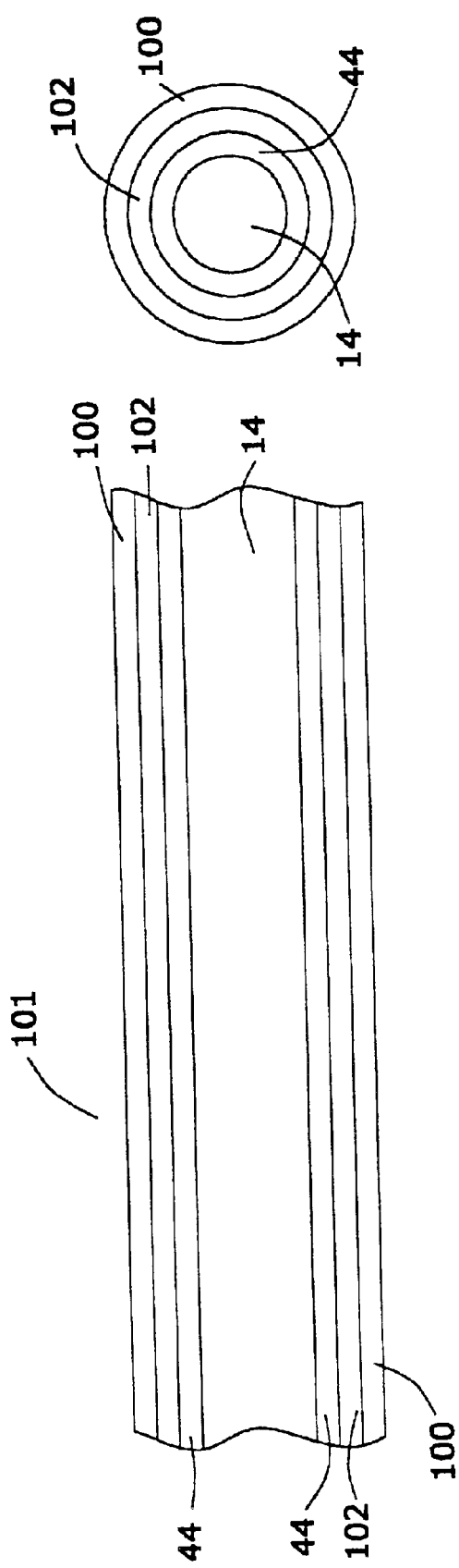
FIGS. 6A and 6B are side and end sectional views of another preferred conductor assembly of this invention.

FIGS. 6A and 6B are side and end sectional views of another preferred conductor assembly 101 of this invention. The assembly 101 is similar in configuration to the assembly 11 but differs therefrom in that only one conductor 14 is utilized. Disposed around conductor 14 are a layer of insulating material 44, a layer of nanoelectrial material 102, and a layer of nanomagnetic material 100.

The layer of nanoelectrical material 102 preferably has a thickness of from about 0.5 to about 2 microns. The nanoelectrical material comprising layer 102 has a resistivity of from about 1.6 to about 100 microohm-centimeters. As is known to those skilled in the art, when nanoelectrical material is exposed to electromagnetic radiation, and in particular to an electric field, it will shield the substrate over which it is disposed from such electrical field. Reference may be had, e.g., to International patent publication WO9820719 in which reference is made to U.S. Pat. No. 4,963,291; each of these patents and patent applications is hereby incorporated by reference into this specification.

As is disclosed in U.S. Pat. No. 4,963,291 of Bercaw, one may produce electromagnetic shielding resins comprised of electroconductive particles, such as iron, aluminum, copper, silver and steel in sizes ranging from 0.5 to 0.50 microns. The entire disclosure of this United States patent is hereby incorporated by reference into this specification.

The nanoelectrical particles used in this invention preferably have a particle size within the range of from about 1 to about 100 microns, and a resistivity of from about 1.6 to about 100 microohm-centimeters. In one embodiment, such nanoelectrical particles comprise a mixture of iron and aluminum. In another embodiment, such nanoelectrical particles consist essentially of a mixture of iron and aluminum. It is preferred that, in such nanoelectrical particles, and in one embodiment, at least 9 moles of aluminum are present for each mole of iron. In another embodiment, at least about 9.5 moles of aluminum are present for each mole of iron. In yet another embodiment, at least 9.9 moles of aluminum are present for each mole of iron.

Figures 7A, 7B:
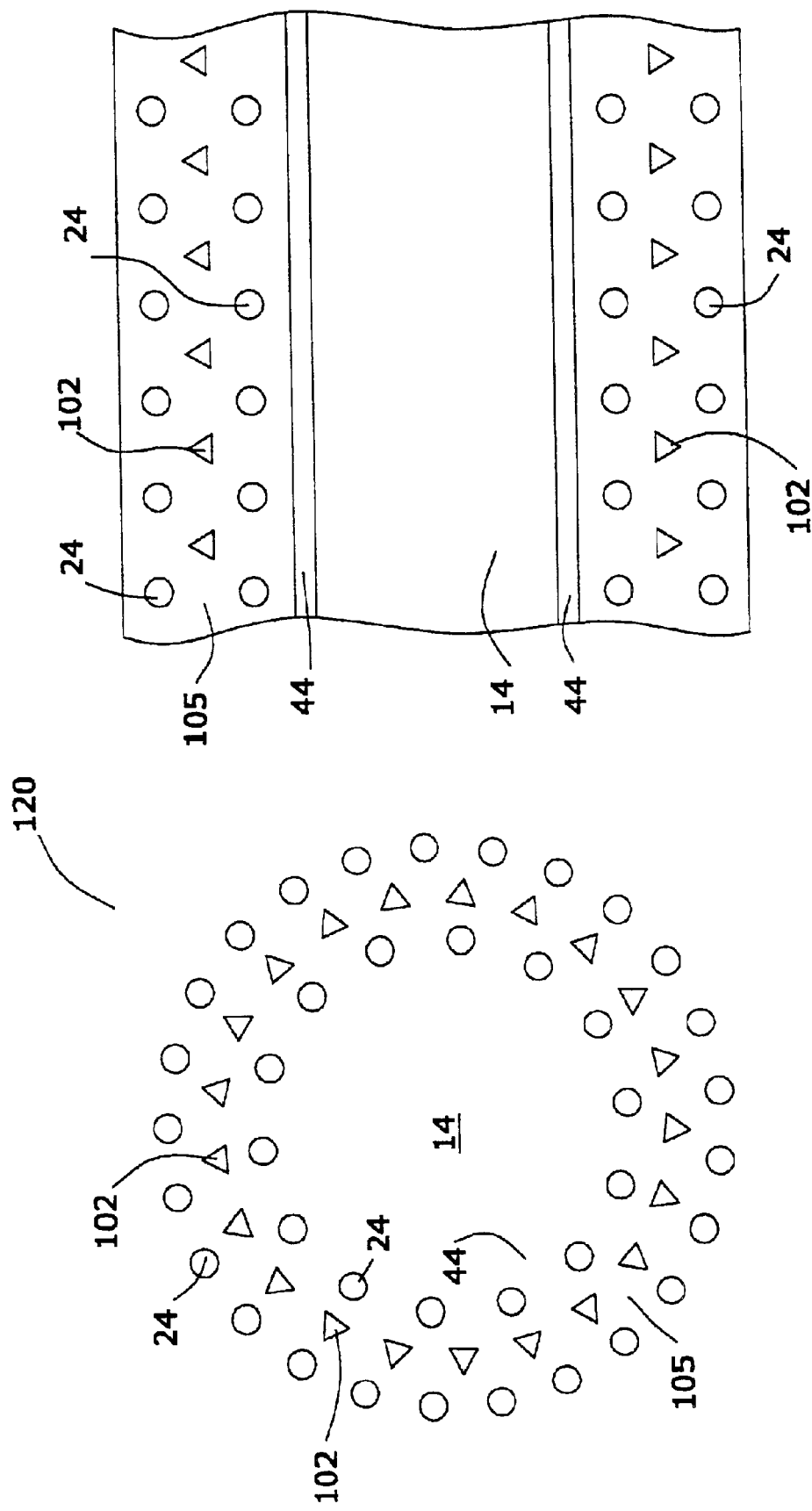
FIGS. 7A and 7B are end and side sectional views of yet another preferred conductor assembly of this invention.

FIGS. 7A and 7B are end and side sectional views of conductor assembly 120 that is similar to the assembly 101 (see FIGS. 6A and 6B) but differs therefrom in that the nanoelectrical material and the nanomagnetic material are both disposed in the same layer 105. One may produce such a layer 105 by simultaneously depositing the nanoelectrical particles and the nanomagnetic particles with, e.g., sputtering technology.

Figure 8:
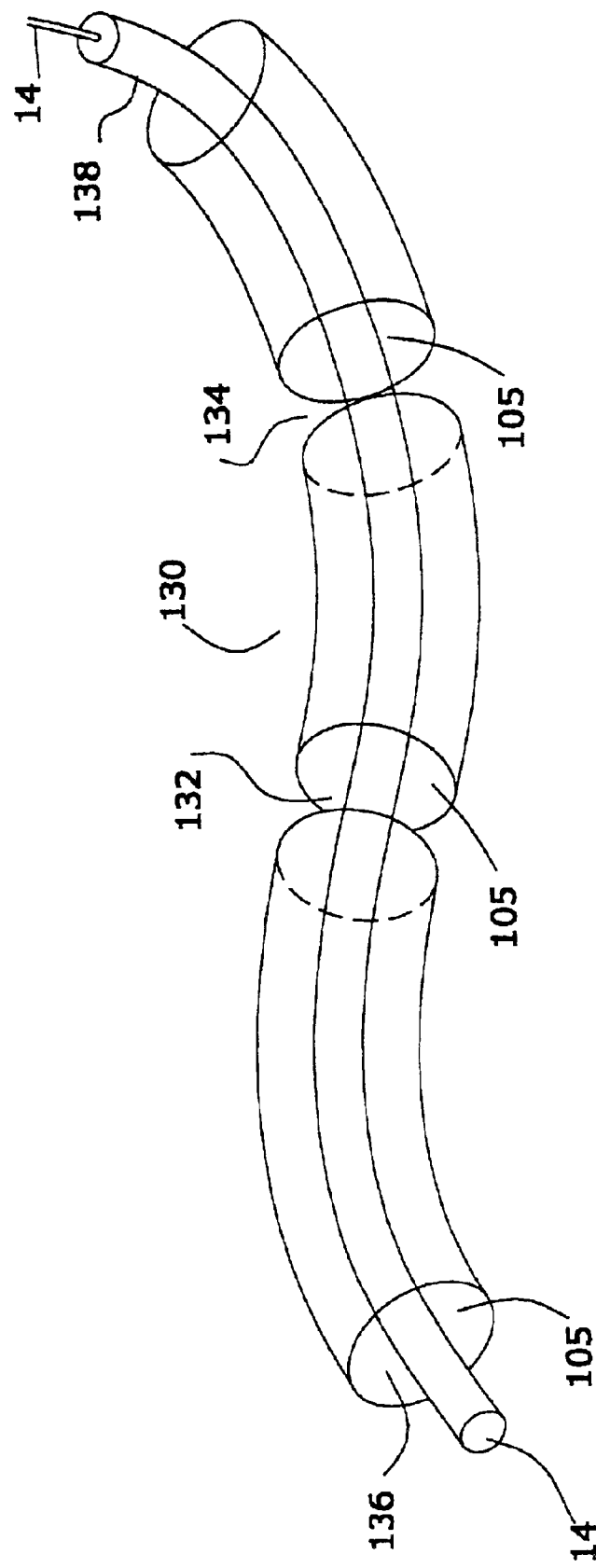
FIG. 8 is a schematic representation of a conductor assembly that is partially coated and partially uncoated.

FIG. 8 is schematic representation of a coated conductor assembly 130 comprised of flexible conductor 14 and coating 105. In the embodiment depicted, the coating 105 contains both nanomagnetic and nanoelectrical particles. In another embodiment, not shown, the coating 105 contains only nanomagnetic particles.

Referring to FIG. 8, it will be seen that sections 134, 134, and 136, and 138 are not coated with the coating 105. The uncoated sections 134 et seq. are less likely to increase their temperature upon being exposed to electromagnetic radiation and, thus, can more readily be contacted with the tissue of a biological organism.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

Thus, e.g., although one embodiment of the process of this invention has been illustrated with regard to two separate, non-contiguous conductors 14 and 16, such process will also function with two contiguous conductors.

I claim:

1. A magnetically shielded conductor assembly comprised of a conductor disposed within an insulating matrix, nanomagnetic material disposed around said conductor, and nanoelectrical material disposed around said conductor, provided that such nanomagnetic material is not contiguous with said conductor, and further provided that such nanoelectrical material is not contiguous with said conductor, wherein:

(a) said conductor has a resistivity of from about 1 to about 100 micro ohm-centimeters, (b) said insulating matrix is comprised of nano-sized particles, wherein at least about 90 weight percent of said particles have a maximum dimension of from about 10 to about 100 nanometers;

(c) said insulating matrix has a resistivity of from about 1,000,000,000 to about 10,000,000,000,000 ohm-centimeter;

(d) said nanomagnetic material has an average particle size of less than about 100 nanometers;

(e) said nanomagnetic material has a saturation magnetization of from about 200 to about 26,000 Gauss and a thickness of less than about 2 microns;

(f) said nanoelectrical material has a resisitivity of from about 1.6 to about 100 microohm-centimeters; and (g) said magnetically shielded conductor assembly is flexible, having a bend radius of less than 2 centimeters.

2. The magnetically shielded conductor assembly as recited in claim 1, wherein said magnetically shielded conductor assembly further comprises a layer comprised of said nanomagnetic material disposed around said conductor, and a layer of said nanoelectrical material disposed around said conductor.

3. The magnetically shielded conductor assembly as recited in claim 1, wherein disposed around said conductor is a layer comprised of said nanomagnetic material and said nanoelectrical material.

4. The magnetically shielded conductor assembly as recited in claim 1, wherein said nanoelectrical material is comprised of aluminum and iron.

5. The magnetically shielded conductor assembly as recited in claim 4, wherein said nanoelectrical material consists essentially of aluminum and iron.

6. The magnetically shielded conductor assembly as recited in claim 5, wherein at least 9 moles of aluminum are present for each mole of iron in said nanoelectrical material.

7. The magnetically shielded conductor assembly as recited in claim 1, wherein said conductor and said second conductor consists essentially of copper.

8. The magnetically shielded conductor assembly as recited in claim 1, wherein said nanomagnetic material is comprised of atoms of iron.

9. The magnetically shielded conductor assembly as recited in claim 1, wherein said nanomagnetic material is comprised of atoms of cobalt.

10. The magnetically shielded conductor assembly as recited in claim 1, wherein said nanomagnetic material is comprised of atoms of nickel.

11. The magnetically shielded conductor assembly as recited in claim 1, further comprising a power supply operatively connected to said conductor.

12. The magnetically shielded conductor assembly as recited in claim 11, wherein said power supply is magnetically shielded.

13. The magnetically shielded conductor assembly as recited in claim 12, wherein said power supply is coated with a layer of nanomagnetic particles.

14. The magnetically shielded conductor assembly as recited in claim 1, further comprising a load connected to said magnetically shielded conductor assembly.

15. The magnetically shielded conductor assembly as recited in claim 14, further comprising a controller connected to said load.

16. The magnetically shielded conductor assembly as recited in claim 15, wherein said controller is connected to said power supply.

17. The magnetically shielded conductor assembly as recited in claim 16, comprising means of delivering pulses of direct current from said power supply to said load.

18. The magnetically shielded conductor assembly as recited in claim 17, wherein said load is magnetically shielded.

19. The magnetically shielded conductor assembly as recited in claim 18, wherein said load is a pacemaker.

* * * * *